United States Patent [19]

Weightman et al.

[11] Patent Number: 4,908,034
[45] Date of Patent: Mar. 13, 1990

[54] ENDOPROSTHETIC BONE JOINT COMPONENTS

[75] Inventors: Barry O. Weightman, Thames Ditton; Robert A. Wordsworth, Bickley, both of England

[73] Assignee: National Research Development Corporation, London, England

[21] Appl. No.: 314,285

[22] Filed: Feb. 23, 1989

Related U.S. Application Data

[63] Continuation of Ser. No. 940,164, Dec. 9, 1986, abandoned, which is a continuation of Ser. No. 676,282, Nov. 29, 1984, abandoned.

[30] Foreign Application Priority Data

Dec. 1, 1983 [GB] United Kingdom ............... 8332119

[51] Int. Cl.⁴ .......................... A61F 2/30; A61F 2/36
[52] U.S. Cl. ........................................ 623/23; 623/18; 623/66
[58] Field of Search ................ 623/22, 23, 18, 19, 623/20, 16, 66

[56] References Cited

U.S. PATENT DOCUMENTS

| 222,825 | 12/1879 | Isham | 403/372 |
|---|---|---|---|
| 1,732,657 | 10/1929 | Picquerez | 403/372 |
| 3,338,600 | 8/1967 | Wahl | 403/372 |
| 3,919,725 | 11/1975 | Swanson et al. | 3/1.91 |
| 4,170,794 | 10/1979 | Zeibig et al. | 623/23 |
| 4,170,794 | 10/1919 | Zeibig et al. | 623/23 |
| 4,227,265 | 10/1980 | Frey | 128/92 CA |

FOREIGN PATENT DOCUMENTS

| 2493139 | 5/1982 | France | 3/1.913 |
|---|---|---|---|
| 1334584 | 10/1973 | United Kingdom | 623/23 |
| 1340436 | 12/1973 | United Kingdom | 623/78 |

Primary Examiner—Richard J. Apley
Assistant Examiner—David J. Isabella
Attorney, Agent, or Firm—Cushman, Darby & Cushman

[57] ABSTRACT

An endoprosthetic bone component is produced from parts respectively having a projection and cavity engaged in a mutual clearance fit, and a third part of plastics material located in the space of such fit, the space and third part being dimensioned to inhibit ejection of the latter and to lock the two parts against mutual articulation during post-operative use. Normally the space and third part will be of generally uniform thickness overall which is small compared to that of the projection. Also the projection and cavity are preferably of uniform cross-sectional shape over at least major portions thereof. Typically the two parts will be of different materials, such as ceramic and metal, suited respectively to articulation and bone fixation roles.

5 Claims, 1 Drawing Sheet

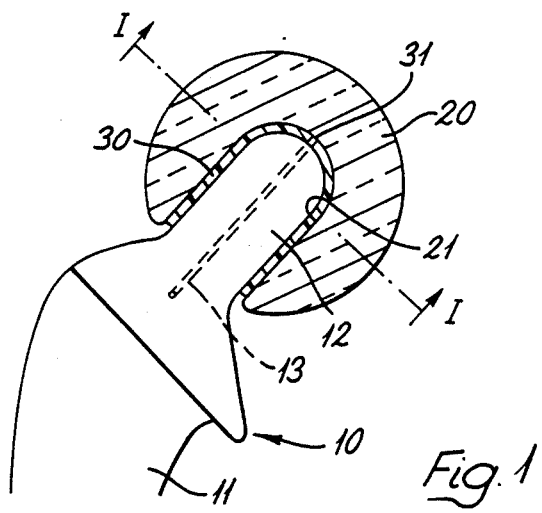
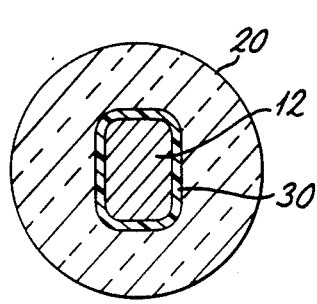
Fig. 2a
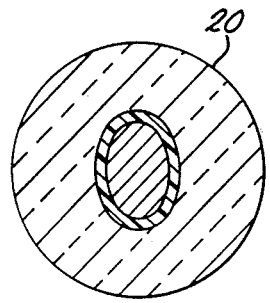
Fig. 2b
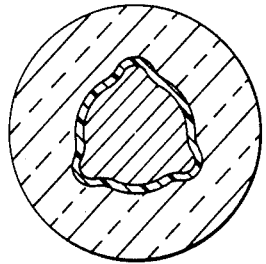
Fig. 2c
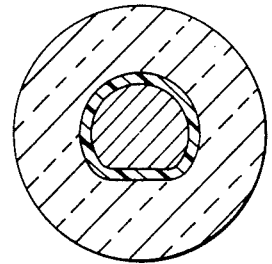
Fig. 2d

ENDOPROSTHETIC BONE JOINT COMPONENTS

This is a continuation of application Ser. No. 06/940,164, filed Dec. 9, 1986, which was abandoned upon the filing hereof; which was a continuation of application Ser. No. 06/676,282, filed Nov. 29, 1984, abandoned.

This invention has been conceived initially in relation to endoprosthetic bone joint components of the kind comprising two parts interconnected in mutually non-articulatory manner, one part defining an articulatory surface for the joint in question, the other part being adapted for fixation in bone, and the two parts being made of respectively different materials selected to suit the relevant articulation and fixation requirements. Typically these requirements respectively involve selection for wear and fatigue resistance.

More specifically the initial concept concerned a commonly-available example of this kind of component involving ceramic and metal for replacing the femoral head in the hip joint. Such a femoral component comprises a ceramic part in the general form of an articulatory ball having a bore connectable with a complementary spigot projecting in a one-piece construction from the wider end of an elongate metal stem part for intramedullary fixation. Different proposals have been made for interconnection of these parts, such as screwing and/or bonding, but the conventional practice is now seen to employ conically shaped surfaces for the bore and spigot which surfaces directly engage in an interference fit.

However, this last practice is far from satisfactory.

Ceramic material is normally produced by a firing process. It is commonly brittle and it is clearly undesirable from a general point of view to form a tapered bore into such material for the purposes of an interference fit which will inherently act like a wedge to cause cracking. More particularly, this action will not be relieved but, on the contrary, will progress towards a maximum because of the circumstances of use. Thus the ceramic part is first subjected during its assembly with the other part to crack propagation stresses which are frozen by virtue of the interference fit, and the ceramic is thereafter repeatedly subjected during post-operative use to body loads by walking and other activity, which loads will progressively tighten the intereference fit and so increase the frozen stresses. In the result the magnitude of the frozen stresses at any time will be proportional to the maximum load ever previously experienced by the component, whether this occurred during assembly, during walking, climbing stairs or other intentional activity, or in a stumble, fall or other unintentional activity.

An attempt is made to form the conical surfaces to very small tolerances for an accurate fit whereby the stresses are distributed uniformly and this may be thought to ameliorate the prospective difficulty of crack propagation from frozen stresses. However, this involves extensive carefully controlled grinding of the bore in the ceramic and adds significantly to production costs. Moreover such grinding is not wholly beneficial, even if the added cost is ignored, because the grinding itself can produce defects which may initiate crack propagation. In this connection it is to be noted that some ceramic parts in current usage can be shown to have a means fracture strength of 45 kN when formed for an optimum interference fit, but commercially-available products are said to have a lesser means strength of 35 kN with currently standard tolerances of fit, and this means that some products will have a strength approaching only one half of the maximum possible and a correspondingly reduced useful life.

These questions of frozen stresses and crack propagation cannot be underestimated because the time-to-fracture of a ceramic part depends upon the level of stress to which it is subjected as well as the time for which the stress acts.

Other examples of the kind of component under discussion are also found among femoral head replacements having head and stem parts of different metals, such as of chrome-cobalt and titanium forms, respectively, which are welded together or are connectable by way of a tapered interference fit. These examples will also normally be more expensive than may otherwise be the case for a unitary component of a single material.

In fact a tapered interference fit is now seen to be deployed as a basis for modular component systems whereby component parts selected from ranges thereof can be connected to provide an overall component involving a beneficial combination of materials and/or a particular configuration suited to an individual patient.

An object of the invention is to improve the general situation discussed above and, to this end, provides a method of producing an endoprosthetic bone component, comprising:
  providing two parts of material substantially non-deformable under body load;
  forming one of said parts with a cavity, and the other of said parts with a projection, said cavity and projection being engageable with a space therebetween in a mutual clearance fit;
  providing a third part of plastics material to fill said space; and
  assembling said component by engaging said cavity and projection and locating said third part in said space;
  said cavity and third part being dimensioned to inhibit ejection of the material of the latter from the former, and also to lock said two parts against mutual articulation, during post-operative use of said component.

The plastics material of the third part, and its shaping or mode of location, is to be such as to allow intimate accommodation to the surfaces of the projection and cavity including geometrical imperfections of very small size relative to the overall dimensions of the surfaces engaged thereby. Moreover, the effect of loads on the component during post-operative use will be such as to pressurise the plastics material to flow into complete accommodation with any surface irregularities of the cavity and projection. This results in a very uniform distribution of load at the materials interfaces and creates mechanical bonds at these interfaces which inhibit mutual articulation between the various parts. This last result is in fact completely contrary to the normal usage of plastics materials in endoprosthetic bone joint devices to provide a low friction articulation capability in association with a different material.

One advantage of the invention is that because there is no reliance on a tapered interference fit, there need be no frozen stresses. A tapered interference-fitted ceramic head is subjected for 24 hours a day to approximately 80% of the maximum stresses ever induced in it, whereas with the present invention the head is subject only to stresses related to a current load. Accordingly the time-to-fracture is greatly increased.

Another primary advantage of the invention is that the cavity and projection of the first two parts do not have to be made to a high quality finish by grinding and/or polishing. This has clear pertinence to a ceramic part which can be used with an as-fired cavity. This advantage is also evident in the avoidance of any need for special connection measures such as welding between parts of different metals.

The plastics material should be creep-resistant to the extent that escape of the material by creep or extrusion from its location between the first two parts is clearly undesirable. Any tendency to such escape normally will be obviated by making the third part, compared to the diameterr of the projection, and the space to be filled thereby, of a generally uniform and small thickness overall. In this connection a thickness of about 0.5 mm has been found suitable for a projection diameter of 15 mm, and proportionate variation appropriate to other sizes.

Plastics materials suitable for the present purpose are in fact already in established use in the prosthetics art, such as ultra high molecular weight polyethylene and polypropylene.

The presently proposed device can be provided in two ways: the plastics part can be preformed for assembly of the device as a push fit, or the plastics part can be formed in situ between the other two parts during assembly.

In the first case there is an additional advantage in that interchangeably connectable parts can be produced to allow selection by the surgeon. For example selection can be made from a range of femoral head sizes for connection with one or more stems. Also revision surgery is facilitated such as by interchange of a larger femoral head in a partial hip prosthesis to a smaller head in a total prosthesis, the two parts being separable by distraction with a suitable tool notwithstanding the mutual non-articulation when assembled.

In the second case there is an advantage in that the desired fluent intimate accommodation of the plastics part to the other parts is effectively ensured by injection of the plastics material in situ. Also, the use of more complex interconnection geometry is facilitated in case this is considered appropriate to ensure mutual non-articulation, this being desirable to avoid wear in the relatively thin plastics material.

In both cases it will be appropriate normally to provide at least one passageway through the preformed parts for escape of air and/or injection of plastics material during assembly. Also, at least in the first case, it may be appropriate following assembly to plug any such passageway, suitably with further plastics material, although this can occur automatically with in situ plastics formation.

While the above discussion of the present invention is thought to be adequate, it may be useful to clarify the same further by way of example with reference to the drawings, in which:

FIG. 1 partially illustrates in schematic cross-sectional view a femoral head replacement component according to the invention, and FIG. 2 shows in transverse cross-sectional views (a) to (d) four respectively different modifications of FIG. 1 at I—I.

The component of FIG. 1 comprises an assembly of first, second and third parts respectively denoted 10, 20 and 30.

The first part 10 is of one-piece metal construction including an elongate tapered stem 11 of which only the wider end is shown, and from which end projects generally axially a spigot 12 of circular cylindrical shape terminating at its free end in a hemisphere. The spigot 12 is formed with a very narrow passageway 13 extending axially therethrough from its free end to emerge radially adjacent the wider end of the stem 11.

The second part 20 is a spherical ball of ceramic material and formed with a cavity 21 of stopped bore form of similar shape to, but sightly larger size than the spigot which is freely receivable therein.

Lastly in respect of the ball, the outer spherical surface is ground and polished to a suitable finish for the purpose of mutual articulation with an acetabular cup whereas the surface of the cavity is as-fired.

The third part 30 is of plastics material, such as RCH 1000, preformed to an axially symmetrical cup shape to serve as a push fit intermediary between the spigot and cavity when assembled as illustrated. This part also has a narrow passageway 31 axially through its base which passageway forms a continuation of passageway 13 and serves therewith for escape of air during assembly.

Also it may be appropriate to plug the passageway 13 as a final step in assembly.

The benefits of this component are evident from the earlier discussion above, namely: there is no direct wedging interference fit between the spigot and ball cavity and so no frozen stresses; the cavity is not ground and so the ball is of significantly reduced cost; and loads on the ball at its cavity are distributed over the whole of the cavity surface by the intimate contact adopted by the plastics cup, this effect being enhanced by post-operative use. Also, it is to be noted that any tendency for escape of the plastics material is reduced by the relatively small wall thickness of this material, and any alternative possibility of plastics material escape through the passageway 13 is also reduced by its narrow width.

A component according to FIG. 1 with a ball head of 32 mm diameter, a spigot of 15 mm diameter, and a plastics material thickness of 0.5 mm, is currently undergoing in vitro testing in Ringers solution at body temperature. In impact testing the minimum fracture strength is found to be double that of an equivalent tapered interference-fitted head. No tendency to significant escape of plastics material has arisen during extensive cyclic loading. More specifically, this second test has involved a load variation between 2 and 27 times body weight, compared to a normal variation between 0 and a maximum of about 4 times body weight when ascending stairs, over 10 million cycles which generally equates with 10 years usage. Also, in a third test, the torque required to effect mutual rotary articulation in such a component is found to exceed by a large factor any torque which naturally occurs in normal usage.

The illustrated component is, of course, only one of many variations possible within the invention as discussed more generally above. For example the plastics material can be formed in situ and the transverse cross-sectional form of the interconnection geometry can be non-circular to provide prismatic, ribbed or other shapes acting against mutual rotation, such as shown in FIG. 2.

Also while reference has been made to ceramic/metal and metal/metal material combinations for the first two parts, yet other material combinations may be advantageously deployed by use of the present invention. This possibility is especially relevant to a situation where one of the materials of a combination thought to be useful is not suited to economical and/or conventional interconnection techniques. This may be the case, for example with carbon fibre reinforced carbon or other carbon-based materials which appear to make available desirable properties, such as porosity and bone-like modulus of elasticity, for the purposes of fixation in bone but are possibly not readily connectable with different materials better suited to articulation.

Lastly, while the invention has been described with particular reference to femoral components for hip prostheses, application to other components having articulatory parts of ball or different form is clearly possible.

We claim:

1. A method of producing an endoprosthetic bone component, comprising:
   providing three parts, two such parts being of material non-deformable under patient body load, and the third such part being of plastics material deformable under such load;
   forming one of said two parts with a cavity and the other of said two parts with a projection, said cavity and projection being configured to be engageable in a mutual a non-wedging clearance fit to define therebetween a space of cup shape having uniform wall thickness;
   forming said third part to said cup shape;
   assembling said component by engaging said cavity and projection to form said space, and locating said third part therebetween in said space in direct engagement with said cavity and projection; and
   subjecting said assembled component to said load to engage said cavity and projection further to force said third part plastics material by deformation towards complete accommodation with the surfaces of said cavity and projection thereby to lock by a non-wedging interference fit, absent any other action on, by and between, said two parts, against mutual articulation;
   said wall thickness being sufficiently small to inhibit ejection of said plastics material by creep under said load.

2. A method according to claim 1 wherein said third part is preformed relative to assembly of said component.

3. A method according to claim 1 wherein said cup shape is circular cylindrical.

4. A method according to claim 1 wherein said one part is formed with a surface area of polished finish quality to replace a natural articulation surface in a bone joint, but said cavity and projection surfaces are formed to a lesser quality finish.

5. A method according to claim 1 wherein said one part is made of ceramic produced by a firing process and said cavity surface is retained in as-fired condition.

* * * * *